United States Patent
Tsutsui et al.

(10) Patent No.: US 6,636,308 B1
(45) Date of Patent: Oct. 21, 2003

(54) APPARATUS FOR MEASURING CHARACTERISTICS OF OPTICAL ANGLE

(75) Inventors: Kazunori Tsutsui, Osaka (JP); Koichi Oka, Shiga (JP); Masayoshi Funato, Osaka (JP); Akira Kawaguchi, Kyoto (JP); Tetsuo Hamada, Kyoto (JP); Michio Tsujio, Osaka (JP)

(73) Assignee: Otsuka Electronics Co., Ltd., Osaka (JP)

(*) Notice: Subject to any disclaimer, the term of this patent is extended or adjusted under 35 U.S.C. 154(b) by 0 days.

(21) Appl. No.: 09/554,687

(22) PCT Filed: Nov. 19, 1998

(86) PCT No.: PCT/JP98/05232
§ 371 (c)(1),
(2), (4) Date: May 18, 2000

(87) PCT Pub. No.: WO99/26054
PCT Pub. Date: May 27, 1999

(30) Foreign Application Priority Data

Nov. 19, 1997 (JP) ................................. 9-318758
Nov. 19, 1997 (JP) ................................. 9-318759

(51) Int. Cl.⁷ ................................................ G01N 21/49
(52) U.S. Cl. ..................................... 356/338; 356/336
(58) Field of Search ................................ 356/336, 338, 356/339, 445, 343

(56) References Cited

U.S. PATENT DOCUMENTS 4,606,636 A * 8/1986 Monin et al. ............. 356/338
5,471,299 A * 11/1995 Kaye et al. ............. 356/336

FOREIGN PATENT DOCUMENTS

| JP | 59-122931 | 7/1984 |
| JP | 62-172242 | 7/1987 |
| JP | 63-243840 | 10/1988 |
| JP | 64-029737 | 1/1989 |
| JP | 3-500815 | 5/1989 |
| JP | 2-096636 | 4/1990 |
| JP | 02-223845 | 9/1990 |
| JP | 02-226046 | 9/1990 |

* cited by examiner

*Primary Examiner*—Frank G. Font
*Assistant Examiner*—Layla Lauchman
(74) *Attorney, Agent, or Firm*—Finnegan, Henderson, Farabow, Garrett & Dunner LLP

(57) ABSTRACT

The present invention relates to a light scattering intensity measuring apparatus capable of measuring, as a function of the scattering angle, the intensity of the light scattered from a sample. This apparatus comprises an ellipsoidal mirror 24 for reflecting and condensing the scattered light from a sample 23; an image-forming lens 25 disposed at the condensing point of light reflected by the ellipsoidal mirror 24 for forming, on a camera face, the image formed on the surface of the reflection mirror 24; and a camera 26 for recording the image formed by the image-forming lens 25. The scattered light in a wide angle range can be detected in a very short period of time (FIG. 1).

7 Claims, 15 Drawing Sheets

F I G. 2
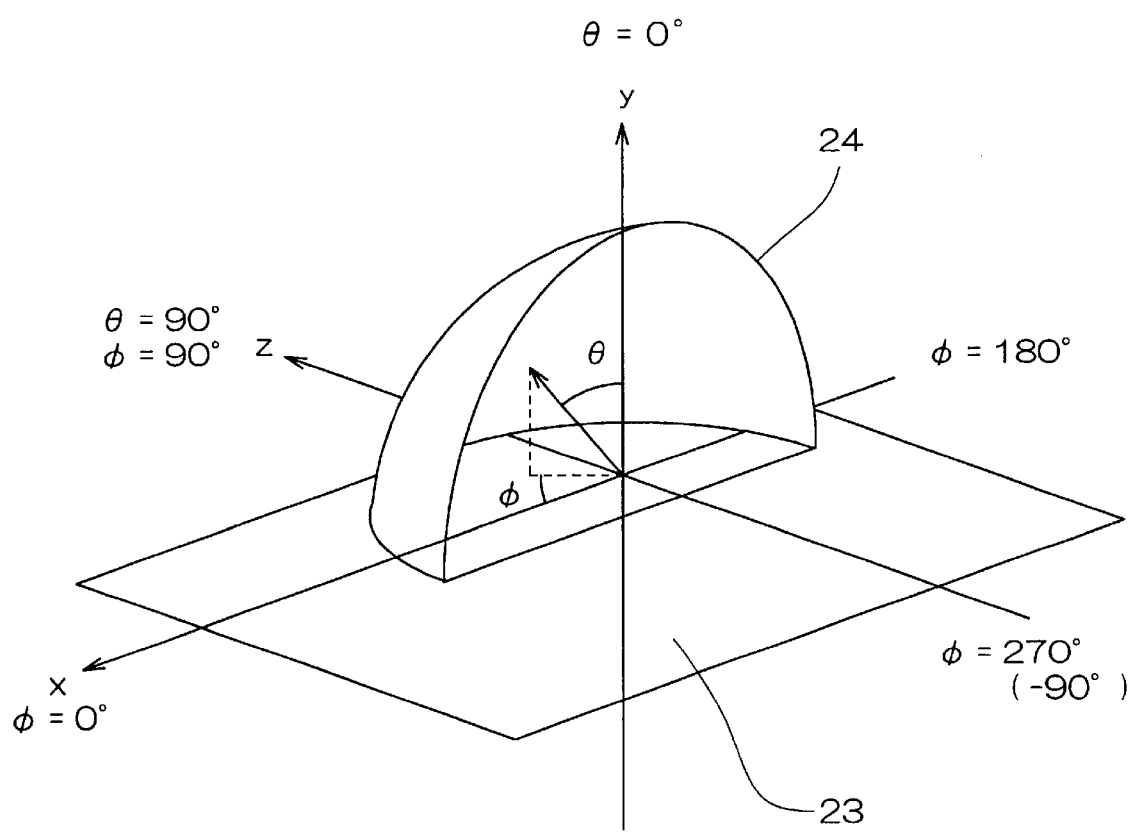

F I G. 8
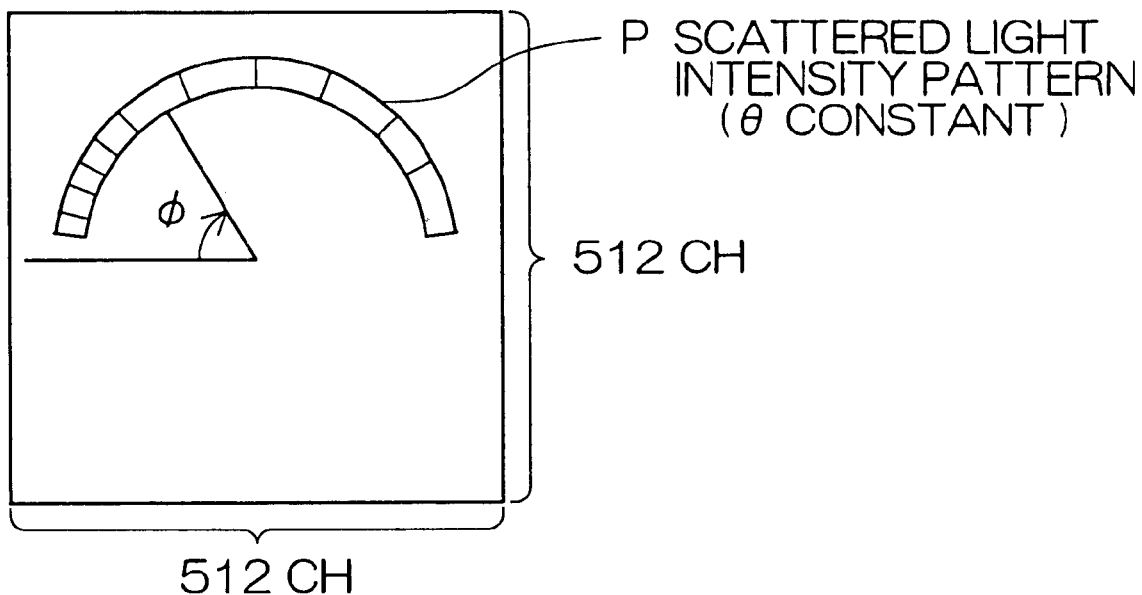

F I G. 10A
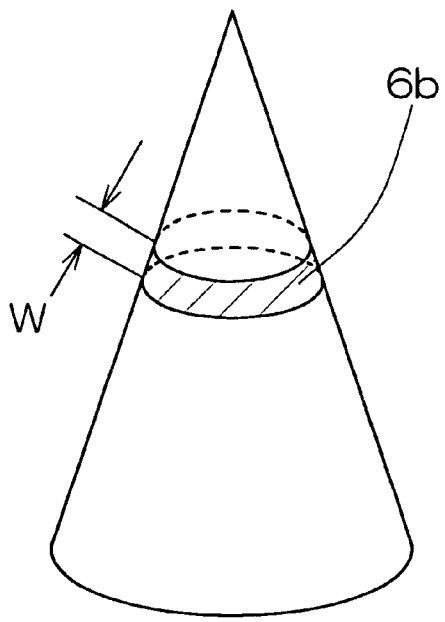
CONICAL BODY
F I G. 10B
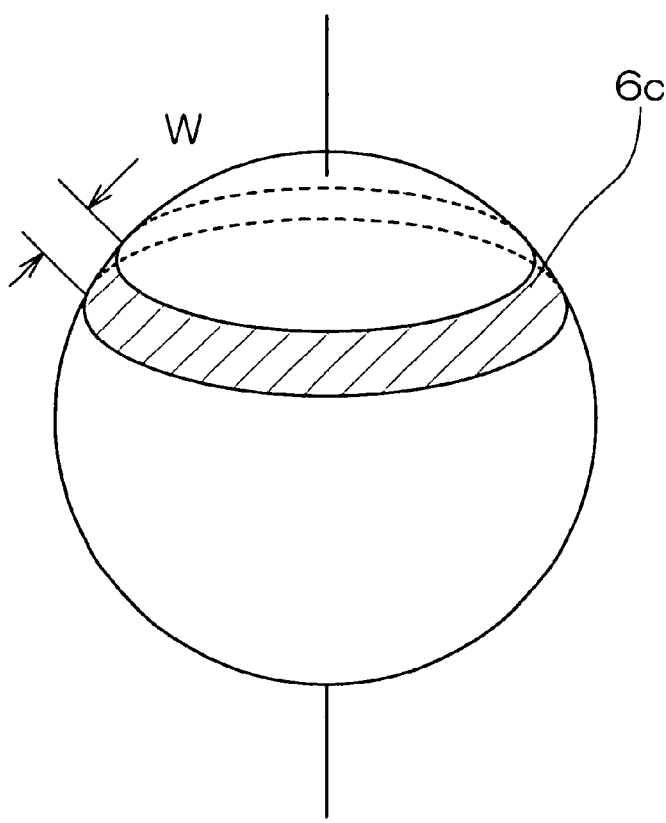
SPHERICAL BODY

APPARATUS FOR MEASURING CHARACTERISTICS OF OPTICAL ANGLE

FIELD OF THE INVENTION

The present invention relates to an optical angle characteristic measuring apparatus capable of measuring, as a function of the angle, the intensity of light emitted from a sample.

DESCRIPTION OF RELATED ART

By irradiating light to a sample and measuring the emitted light for its angle dependency and changes with the passage of time, there can be obtained information of the particles as to sizes, shapes, molecular weights, thermal agitation and the like.

Apparatus for measuring the angle dependency of emitted light is called an optical angle characteristic measuring apparatus. More precisely, apparatus for measuring the angle dependency of scattered light is called a light scattering intensity measuring apparatus. The light scattering intensity measuring apparatus is arranged such that light is irradiated in one direction to a sample, that a detector for detecting the scattered light is disposed on a goniometer rotatable around the sample, and that the scattered light is detected at a variety of angles with the goniometer rotated.

However, when it is intended to measure such scattered light in a wide range of angle with the light scattering intensity measuring apparatus, it takes several tens of minutes or more for measurement. This is disadvantageous in time efficiency. Further, measurement cannot disadvantageously be conducted on a sample which undergoes, within the measuring period of time, changes with the passage of time such as association, cohesion or the like.

For shortening the measuring period of time, it is required to reduce the number of measuring angle points. This sacrifices the data precision.

Further, to prevent the observation point from deviating when the goniometer is rotated, it is required to design apparatus with very high precision. This disadvantageously requires much labor.

In this connection, there is developed apparatus for detecting the scattered light with a plurality of detector fixed in an annular manner around the sample. In this apparatus, however, the number of measuring angles is limited to a certain value.

It is an object of the present invention to provide an optical angle characteristic measuring apparatus for measuring, as a function of the light emitting angle, the intensity of light emitted from a sample, which apparatus is capable of detecting, in a very short period of time, the emitted light in a wide range of angle up to 360°.

SUMMARY OF THE INVENTION (1) According to the present invention, an optical angle characteristic measuring apparatus comprises: a ellipsoidal mirror for reflecting and condensing the emitted light from a sample disposed in the vicinity of the first focal point of the ellipsoidal mirror; image-forming means disposed in the vicinity of the second focal point of the light reflected from said ellipsoidal mirror for forming, on a record face, the image formed on the surface of the ellipsoidal mirror; and record means for recording the image formed by the image-forming means.

According to the arrangement above-mentioned, the image-forming means can form, on a record face, the image formed on the mirror face of the ellipsoidal mirror. Accordingly, the record means can record the intensity pattern of the emitted light.

Thus, the apparatus according to the present invention is different in provision of the image-forming means and the record means from the inventions disclosed in Japanese Patent Laid-Open Publications No. H2-223845 and S64-29737 in each of which a reflection mirror is utilized merely as a kind of an integrating sphere.

According to the optical angle characteristic measuring apparatus of the present invention, the angle dependency data of emitted light can simultaneously be measured in a very wide angle range without the optical system component elements moved. This remarkably improves the measurement in time efficiency. Accordingly, the apparatus of the present invention can measure a sample, undergoing a change with the passage of time, which has conventionally been measured with difficulty. For example, dynamic scattering characteristics can also be measured.

Further, the apparatus of the present invention has no movable members as optical system component elements. This not only improves the measurement in stability and reliability, but also lengthens the lifetime of the apparatus. The number of the optical system component elements is reduced. This is advantageous in view of cost and production efficiency.

Further, according to the arrangement of the present invention, the image formed on the mirror face of the ellipsoidal mirror can be formed on the record face in a stigmatic manner.

The following description will discuss the operation of this optical angle characteristic measuring apparatus with reference to FIG. 1 illustrating a specific arrangement of the present invention.

A sample 23 is disposed in the vicinity of a first focal point of an ellipsoidal mirror 24. Light emitted from the sample 23 is reflected and condensed by the ellipsoidal mirror 24 and then incident upon a camera 26 serving as record means through an image-forming lens 25 disposed at a second focal point of the ellipsoidal mirror 24.

The image formed on the recording face of the camera 26 represents the image formed on the mirror face of the ellipsoidal mirror 24, and corresponds to the emitting angle at which light is emitted from the sample. It is a remarkable feature that because of the nature of an ellipsoidal mirror, this image is an image formed in a stigmatic manner.

FIG. 2 is a view of coordinates illustrating the light emitting angle. As shown in FIG. 2, a plane sample 23 is assumed and the original point is located in a position which serves as the point to be measured on the sample 23. As shown in FIG. 2, there is formed a system of orthogonal coordinates x, y, z in which an angle θ is formed between the light direction and the y-axis and an angle ø is formed between the light image projected on the x-z plane and the x-axis. These angles θ and ø are called visual field angles. A position on the mirror face of the ellipsoidal mirror 24 can be identified by these visual field angles θ and ø.

FIG. 3 is a projection view of the angles θ, ø reflected on the mirror face of the ellipsoidal mirror 24. The real image of this projection view is formed on the recording face of the camera 26 by the operation of the image-forming lens 25.

It is therefore possible to measure the optical characteristics of the sample, according to the visual field angles, such as polarization characteristics, scattering angle characteristics, reflectivity data, transmissivity data, luminance data, chromaticity data and the like. Further, the range of the visual field angles is stigmatic and extends widely from 0° to 90° for θ and from −20° (340°) to 200° for ø as shown in FIG. 3.

It can be considered that the curvature of the ellipsoidal mirror 24 deviates from the ideal one. In this case, the projection view in FIG. 3 becomes different from the calculated distribution. It is therefore required to correct the distribution with the use of a standard sample (for example, a transmission-type grating) of which visual field angles are known.

(2) The ellipsoidal mirror may be replaced by a spherical mirror formed from a portion of a spherical surface or a conical mirror formed from a portion of a conical surface. In such a case, too, the projection view is different from the calculated distribution. It is therefore required to correct the distribution with the use of a standard sample (for example, a transmission-type grating) of which visual field angles are known. The best advantage of the arrangement above-mentioned is that such spherical or conical mirror can more readily be produced as compared with the ellipsoidal mirror.

BRIEF DESCRIPTION OF THE DRAWINGS

FIG. 2 is a view of coordinates illustrating visual field angles;

Each of FIG. 6(A)

FIG. 8 is a view illustrating the scattered light intensity pattern generated on the camera face of a CCD camera;

FIG. 10(A) shows a mirror 6b obtained by cutting a portion of a cone in a round slice, and FIG. 10(B) shows a mirror 6c obtained by cutting a portion of a spherical surface in a round slice;

DESCRIPTION OF THE PREFERRED EMBODIMENTS

The following description will discuss in detail preferred embodiments of the present invention with reference to the attached drawings.

First Embodiment

Figure 1:
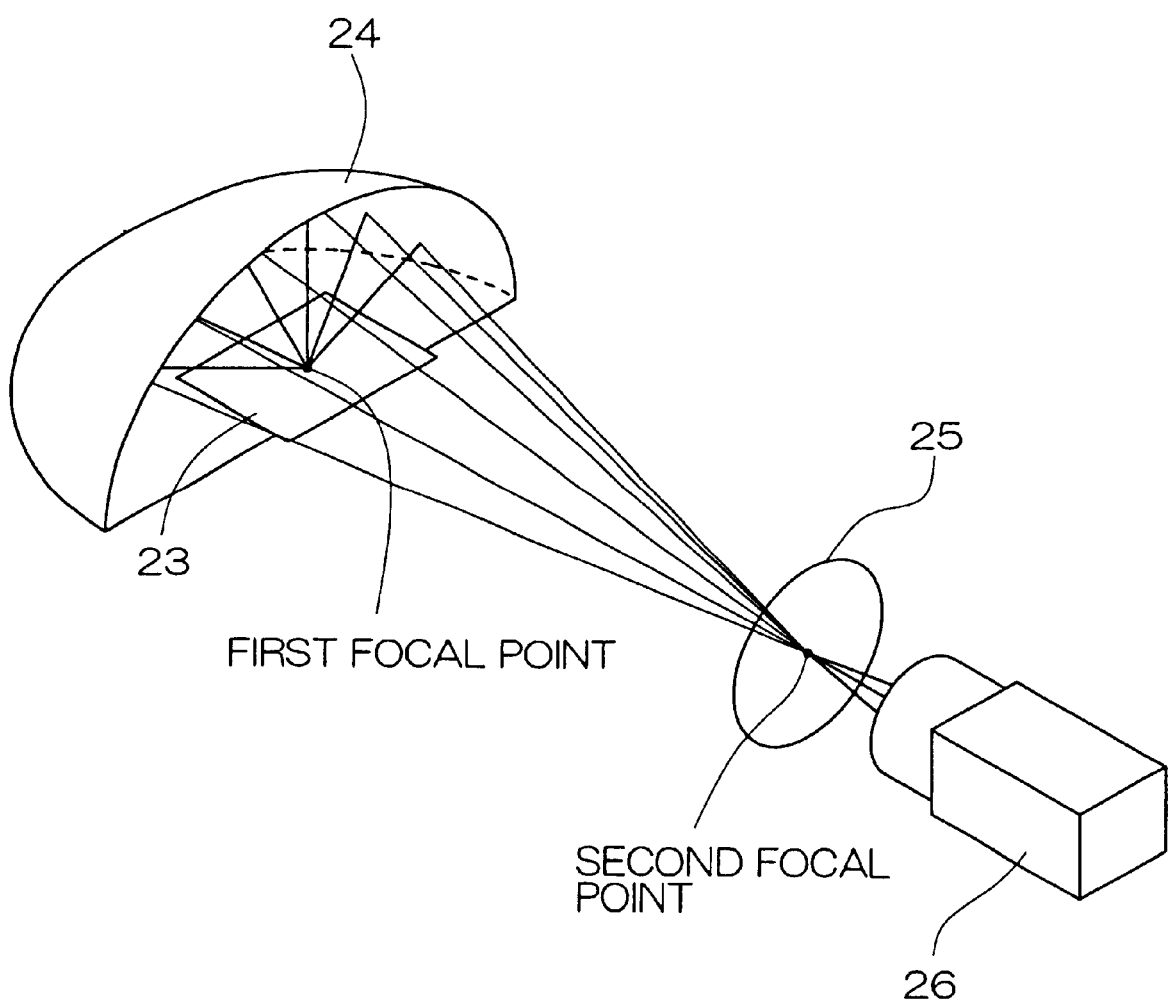
FIG. 1 is a view illustrating the operation of an optical angle characteristic measuring apparatus according to the present invention.
Figure 3:
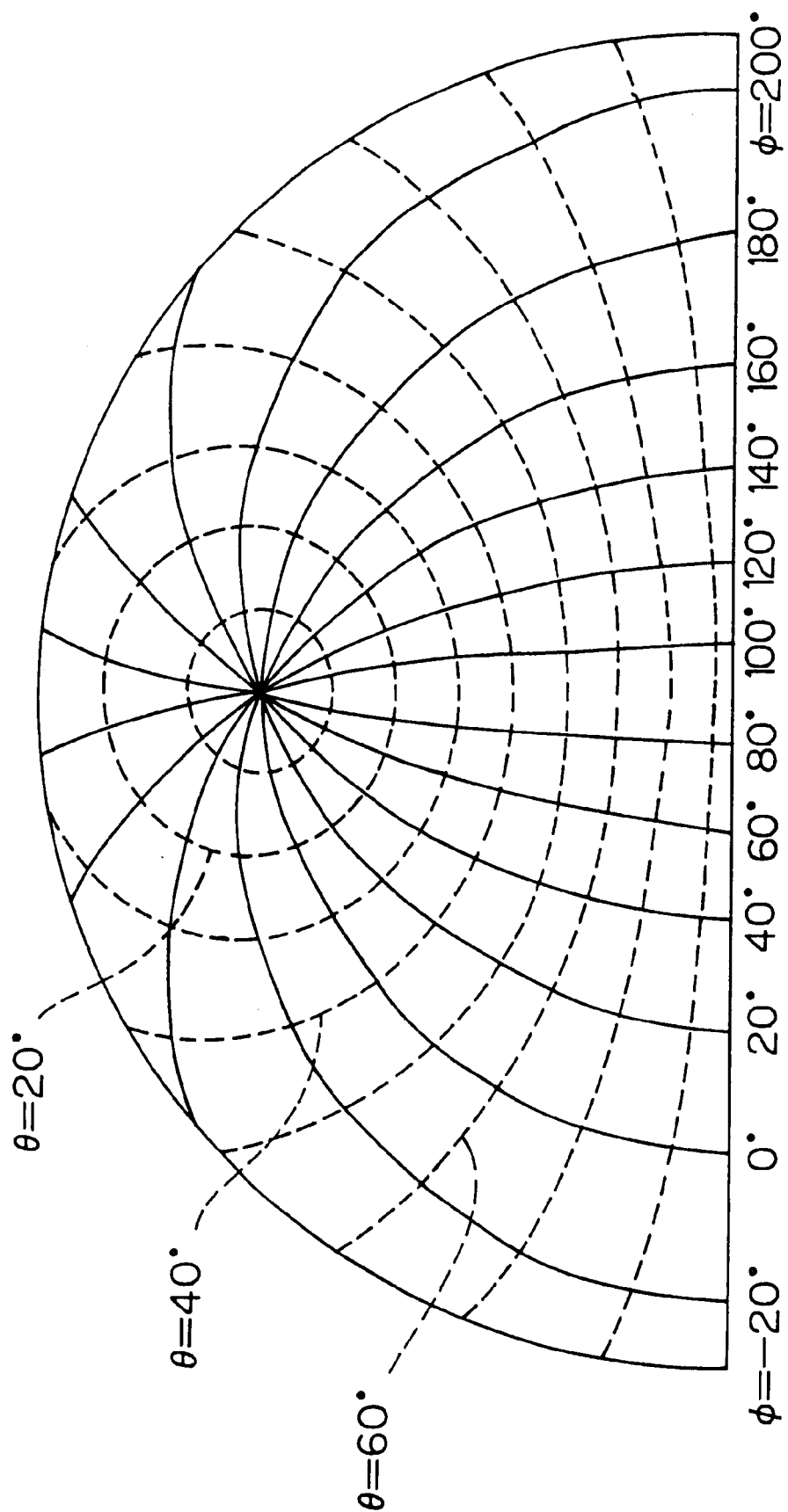
FIG. 3 is a projection view reflected on the mirror face of an ellipsoidal mirror.
Figure 4:
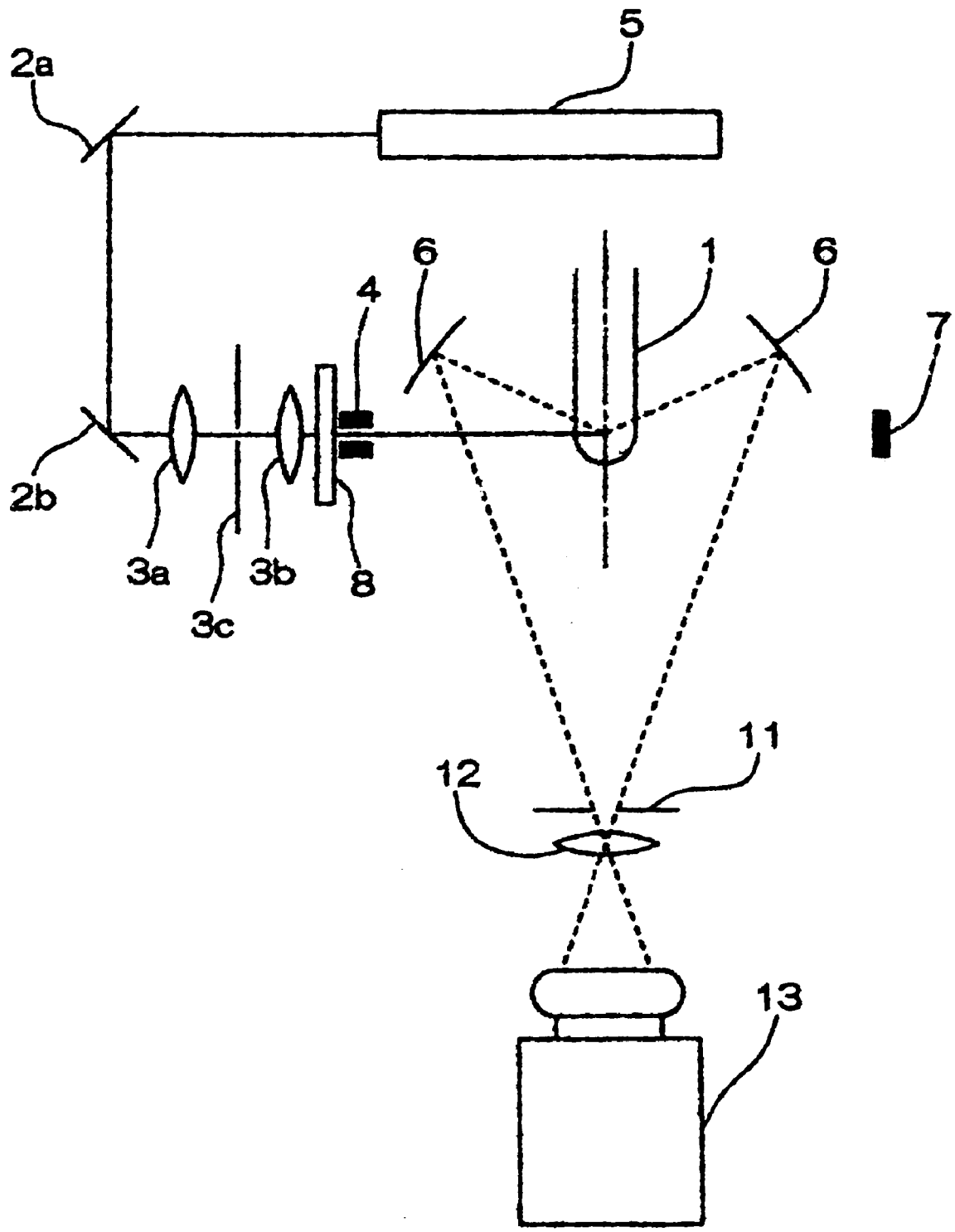
FIG. 4 is a schematic view of a light scattering intensity measuring apparatus.

FIG. 4 is a schematic view of a light scattering intensity measuring apparatus according to the present invention.

The light scattering intensity measuring apparatus comprises a glass-made sample cell 1 for housing a sample to be measured, and a laser device 5 for projecting a laser beam to the sample cell 1 through mirrors 2a, 2b, condensing lenses 3a, 3b, an aperture 3c, a glass window 8 and a pinhole 4. The light scattering intensity measuring apparatus further comprises: an ellipsoidal mirror 6 for condensing the scattered light from the sample on an image-forming lens 12; an aperture 11 through which reflected light from the ellipsoidal mirror 6 passes; the image-forming lens 12; and a CCD camera 13. The image-forming lens 12 is arranged to form, on the camera face of the CCD camera 13, the image formed on the mirror face of the ellipsoidal mirror 6. An absorbing plate 7 is disposed for absorbing the laser beam which has been transmitted straight through the sample cell 1. The absorbing plate 7 prevents the transmitted laser beam from reflecting and scattering after striking against the glass window 8 and the like. The pinhole 4, the aperture 3c and the aperture 11 are disposed for cutting excessive stray light around the laser beam, contributing to the formation of a clean laser beam profile.

In FIG. 4, the laser device 5 is disposed at a position above the sample cell 1 for reasons of drawing a figure in plan elevation. However, as far as light can be incident upon the sample cell 1, the position of the laser device 5 is not limited to the position shown in FIG. 4. For example, the laser device 5 can be disposed at a level identical with that at which the sample cell 1 is disposed (In this case, it is a matter of course that the mirror positions are accordingly changed).

Figure 5:
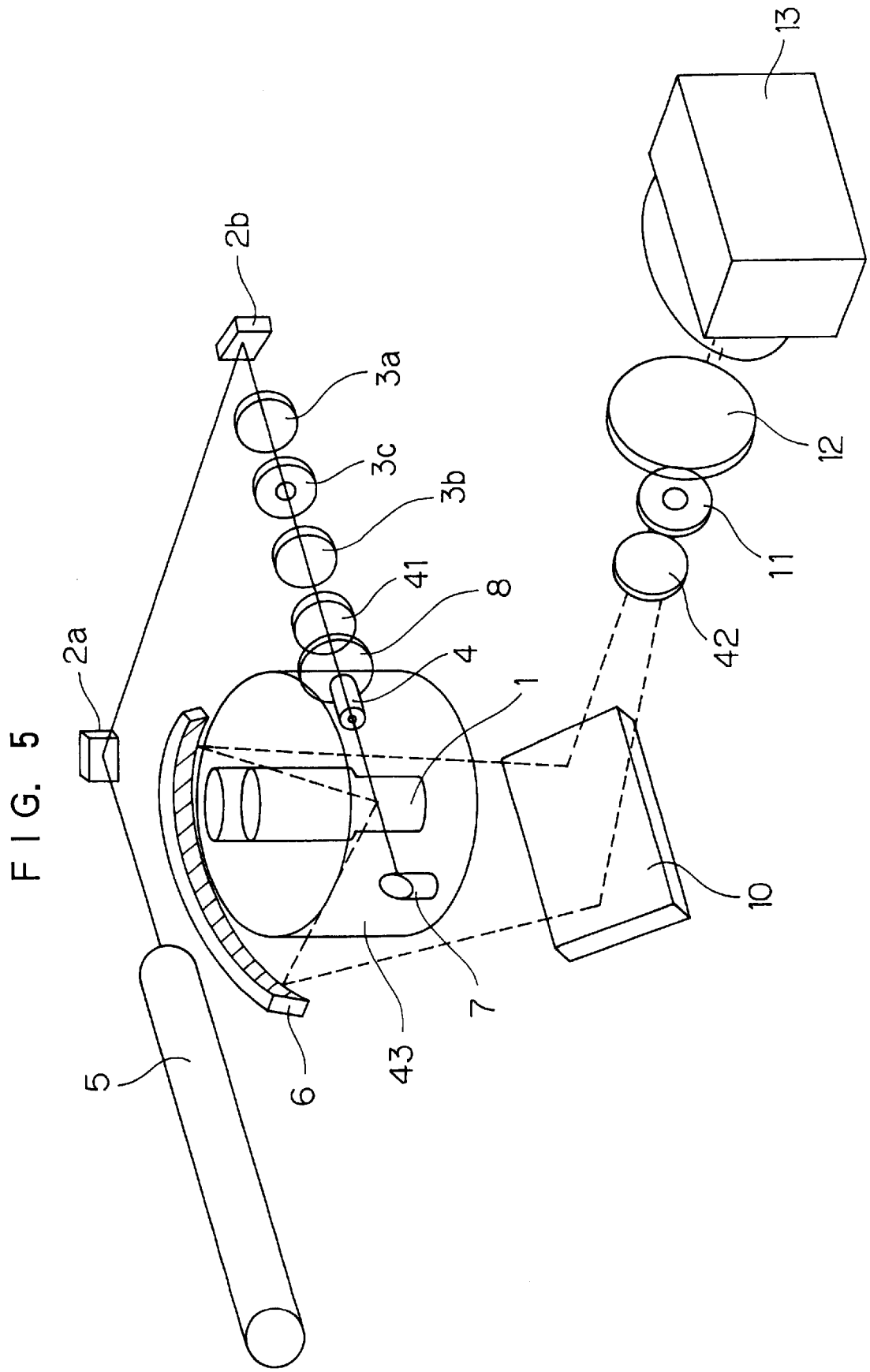
FIG. 5 is a perspective view of a light scattering intensity measuring apparatus.

FIG. 5 is a perspective view of a general arrangement of a light scattering intensity measuring apparatus in which the laser device 5 is disposed at a level identical with that at which the sample cell 1 is disposed. Except for the following points (a) and (b), the arrangement in FIG. 5 is the same as the arrangement in FIG. 4.

(a) A polarizer 41 and an analyzer 42 are added.
(b) The light incident direction with respect to the sample cell 1 is different by an angle of 90°.

The point (a) makes it possible to know the polarization components of the light irradiated to the sample cell 1 and the light scattered from the sample. By evaluating the polarization components, the anisotropy and integrity of the sample can be evaluated. The point (b) is a trivial matter.

Figure 6A:
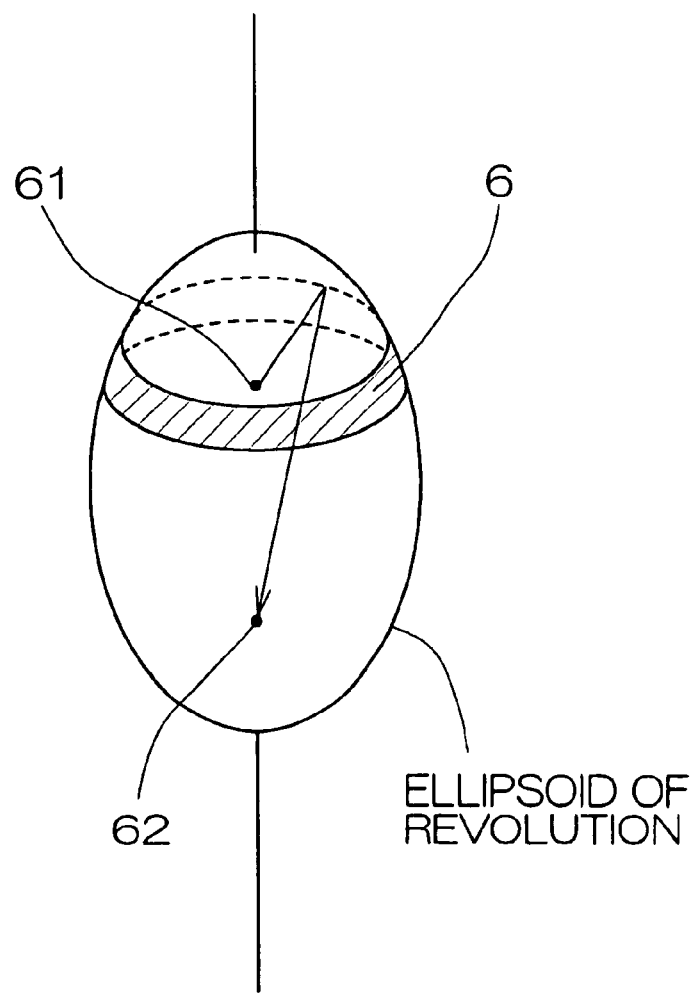
FIG. 6(B) is a view of an ellipsoidal mirror obtained by cutting an ellipsoid of revolution in a round slice of which inner face serves as a mirror face.
Figure 6B:
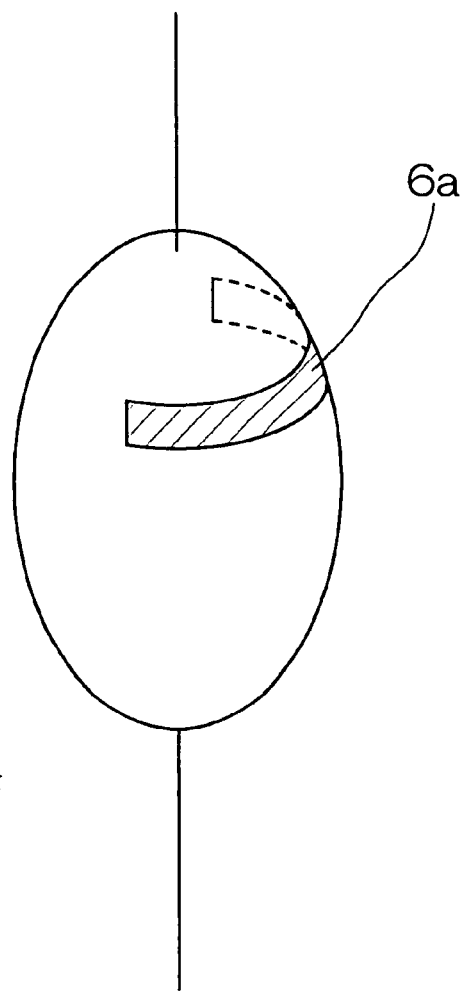

FIG. 6 is a view illustrating the function of the ellipsoidal mirror 6. The ellipsoidal mirror 6 is obtained by cutting the surface of an ellipsoid of revolution in a round slice of which inner face serves as a mirror face. Because of the nature of the ellipsoid of revolution, light from one focal point 61 strikes against the ellipsoidal mirror 6 and converges on the other focal point 62. The ellipsoidal mirror 6 is not always required to be a round circular shape, but may be a partial portion of a round circular piece as shown in FIG. 6(B). It is enough that the mirror is present in the scattering angle range to be measured.

Utilizing the nature of the ellipsoid of revolution, the light scattering intensity measuring apparatus is provided at the one focal point with the sample cell 1 and at the other focal point with the image-forming lens 12. Accordingly, that portion of the scattered light from the sample cell 1 which has struck against the ellipsoidal mirror 6, is reflected thereby and condensed on the image-forming lens 12, and is then incident upon a CCD camera 13.

Figure 7:
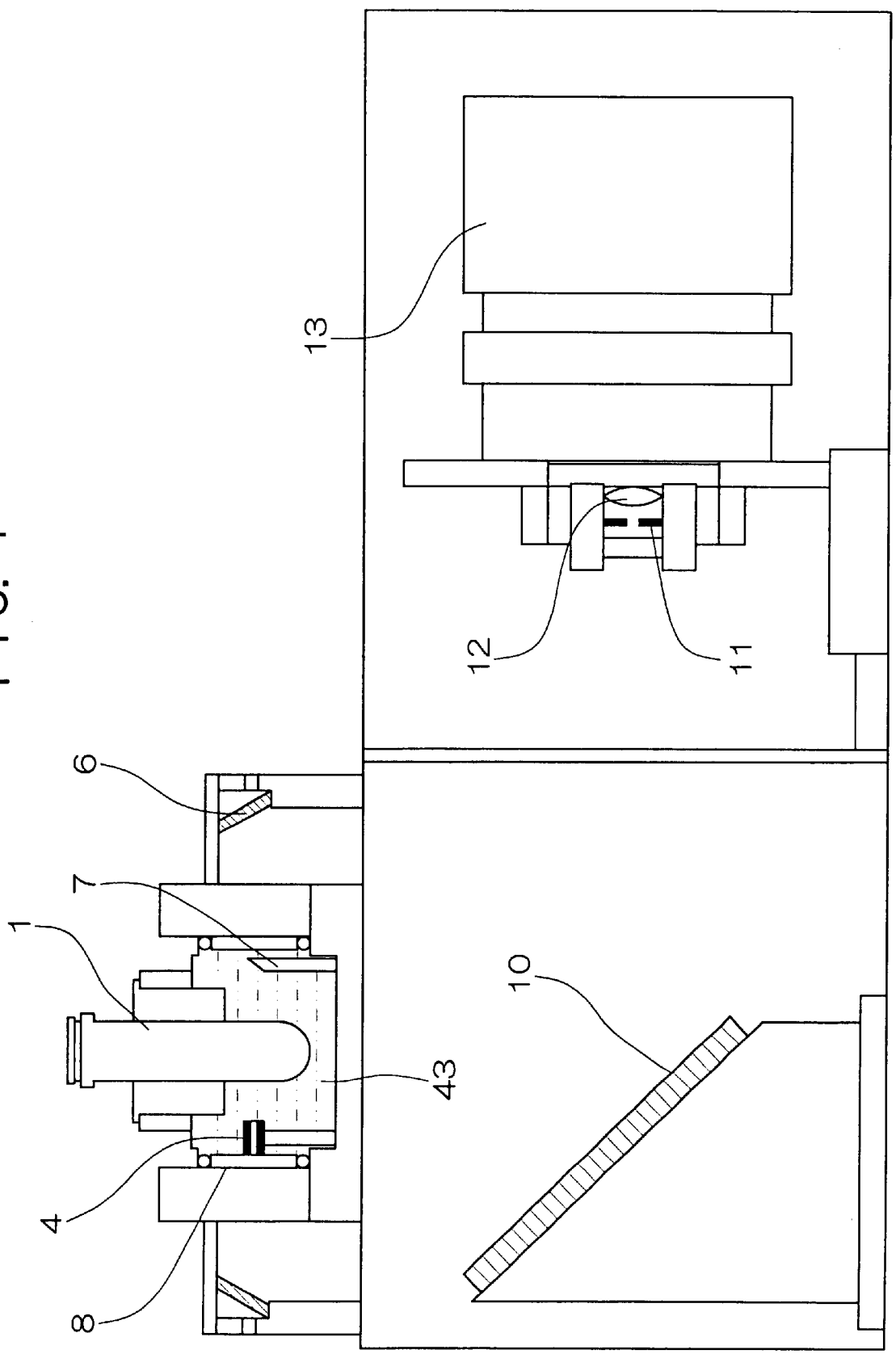
FIG. 7 is a view illustrating a specific structure of a light scattering intensity measuring apparatus.

FIG. 7 shows a view illustrating a specific structure of the light scattering intensity measuring apparatus in FIG. 4. In FIG. 7, there are omitted a laser device for projecting a laser beam to the sample cell 1, a mirror and a condensing lens.

The sample cell 1 is set in a thermostatic liquid immersion bath 43 filled with a liquid presenting the refractive index close to the cell. Scattered light from the sample cell 1 is transmitted through a glass window 8, strikes against the ellipsoidal mirror 6 and is then reflected thereby. Disposed immediately below the sample cell 1 is a plane mirror 10 by which the light reflected by the ellipsoidal mirror 6, is changed in direction. By changing the reflected light in direction, this plane mirror 10 produces an effect of reducing the height of the entire apparatus.

The light changed in direction by the plane mirror 10 is incident upon the CCD camera 13 through the aperture 11 and the image-forming lens 12. The CCD camera 13 uses a light receiving element very high in positional resolution (for example 512×512 pixels). This makes it possible to obtain data with high resolution, i.e., the scattering angle of 1° or less as measuring angle resolution.

Figure 9:
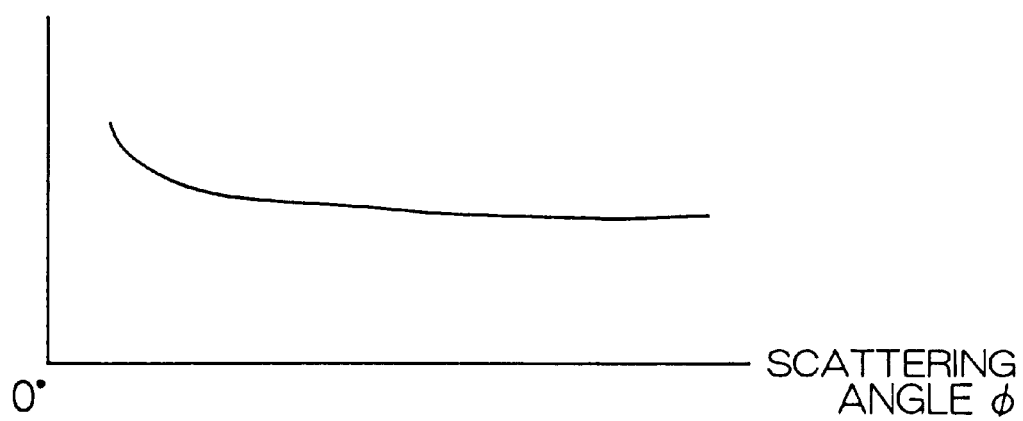
FIG. 9 is a graph illustrating the scattered light intensity pattern as a function of scattering angle ø.

FIG. 8 shows the scattered light intensity pattern generated on the camera face of the CCD camera 13. This scattered light pattern is a pattern formed on the mirror face of the ellipsoidal mirror 6 in the form of a circular arc shown in FIG. 6(B), and covers the scattering angle ø range from 5° to 175°. FIG. 9 shows this pattern in the form of a graph in which the axis of abscissa presents the scattering angle ø.

Thus, without the optical system component elements moved, scattering light intensity data can simultaneously be obtained at optional angles in a wide angle range.

The present invention should not be limited to the embodiment above-mentioned. That is, other mirror than an ellipsoidal mirror may be used for condensing the scattered light from the sample on the image-forming lens 12. For example, there may be used, as such a mirror, a mirror 6b obtained by cutting a portion of a cone in a round slice as shown in FIG. 10(A), or a mirror 6c obtained by cutting a portion of a spherical surface in a round slice as shown in FIG. 10(B). When each of the mirrors 6b, 6c is used, it does not occur that light coming from one focal point and striking against the ellipsoidal mirror 6, is condensed on the other focal point in a stigmatic manner as done with the ellipsoidal mirror 6. However, by reducing the width W of each of the mirrors 6b, 6c, light coming from one focal point and striking against each of the mirrors 6b, 6c, can substantially be condensed upon one point. Accordingly, even the use of each of the mirrors 6b, 6c makes it possible to obtain scattered light data with precision equivalent to that in the case of the use of the ellipsoidal mirror 6.

Second Embodiment

Figure 11:
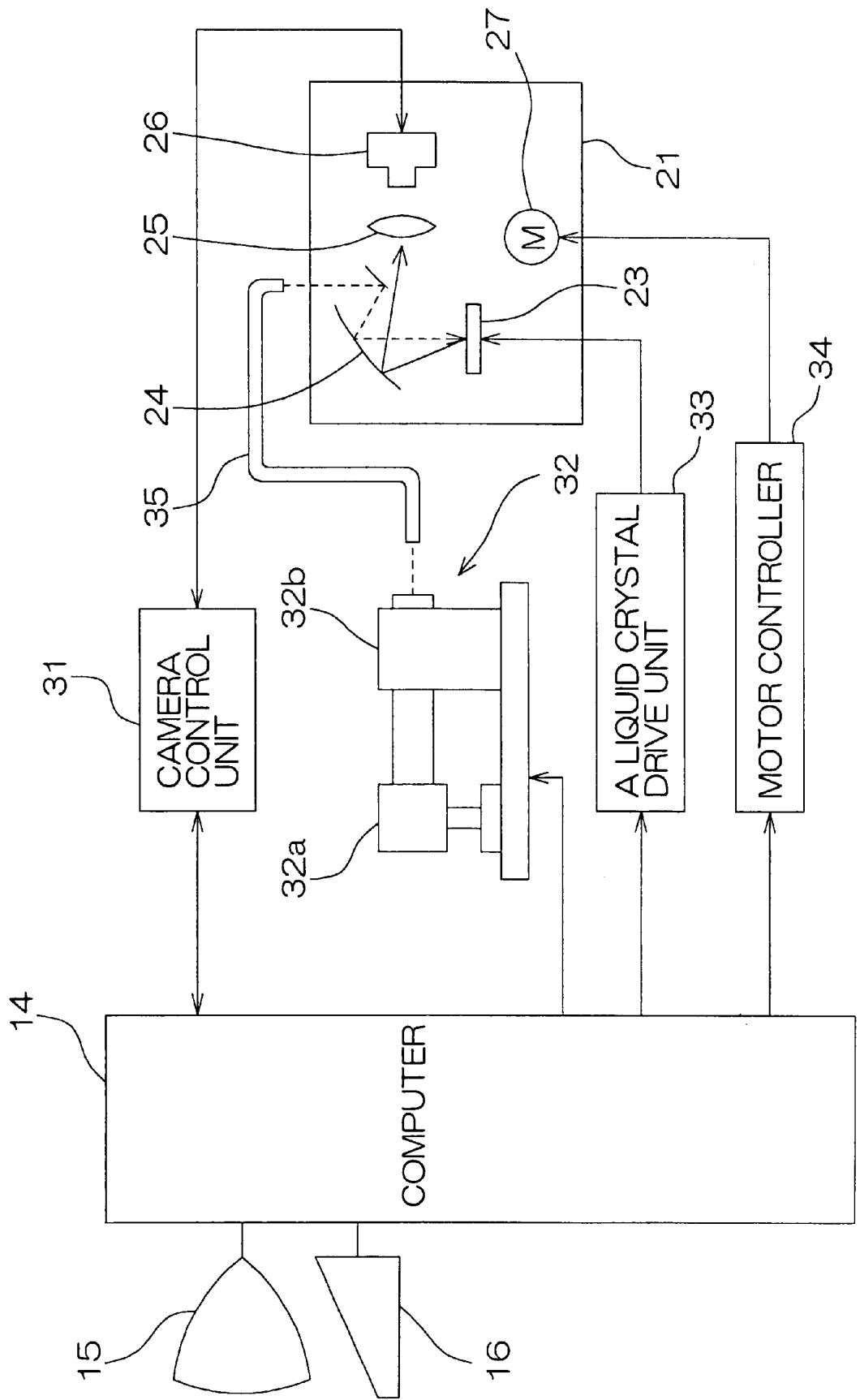
FIG. 11 is a block diagram of a general arrangement of an optical angle characteristic measuring apparatus.

FIG. 11 is a block diagram of a general arrangement of an optical angle characteristic measuring apparatus.

This optical angle characteristic measuring apparatus has an optical system 21 comprising an ellipsoidal mirror of revolution 24, an image-forming lens 25, a camera 26 and motors 27 for operating a variety of movable members.

The optical angle characteristic measuring apparatus further comprises: an illumination light source 32 for generating monochromatic light to be irradiated to a liquid crystal display element 23 as an example of the sample; an optical fiber 35 for guiding light of the illumination light source 32 to the optical system 21 (a mirror system can be used instead of the optical fiber 35); a camera control unit 31 for taking image data from the camera 26 and controlling the parameters such as light exposure time and the like; a liquid crystal drive unit 33 for generating a signal for driving the liquid crystal display element 23; a motor controller 34; a computer 14 for controlling the apparatus in its entirety; a display device 15; and a keyboard 16. It is noted that examples of the sample include, in addition to a liquid crystal display element, a light emitting diode, an optical fiber light emitting end, a film, a color filter and the like.

It is assumed that the illumination light source 32 is a combination of a white-color illumination light source 32a with a monochromator 32b. The selection of the wavelength of the monochromator 32b is controlled by the computer 14 and the like. Instead of the monochromator 32b, there may be used a laser illumination light source, an illumination light source for generating multi-color light instead of monochromatic light, or an illumination light source for generating white-color light such as a halogen lamp, a Xe lamp, a metal halide lamp or the like. More specifically, the type of illumination light source to be used is dependent on the measuring conditions of the sample 23. When the sample is of the self-light-emitting type, the illumination light source 32 may not be used. When a laser illumination light source is used and the emitted light is a linear polarized light, this linear polarized light may be used as converted into a circular polarized light with the use of a ¼-wavelength plate such that the polarization characteristics exert no effect on the measurement.

As the camera 26, there may be used optional means which can store a formed image. For example, there may be used means for converting an image into an electric signal such as a CCD camera, or means for chemically recording an image on a film such as an optical camera. In FIG. 11, it is assumed that a CCD camera is used.

The motors 27 and the motor controller 34 are disposed for controlling the posture of the sample 23 and for rotating, moving and operating a variety of optical elements such as the shaft for irradiating light to the sample 23, a polarizer, an analyzer, a phase-contrast plate and the like.

Figure 12:
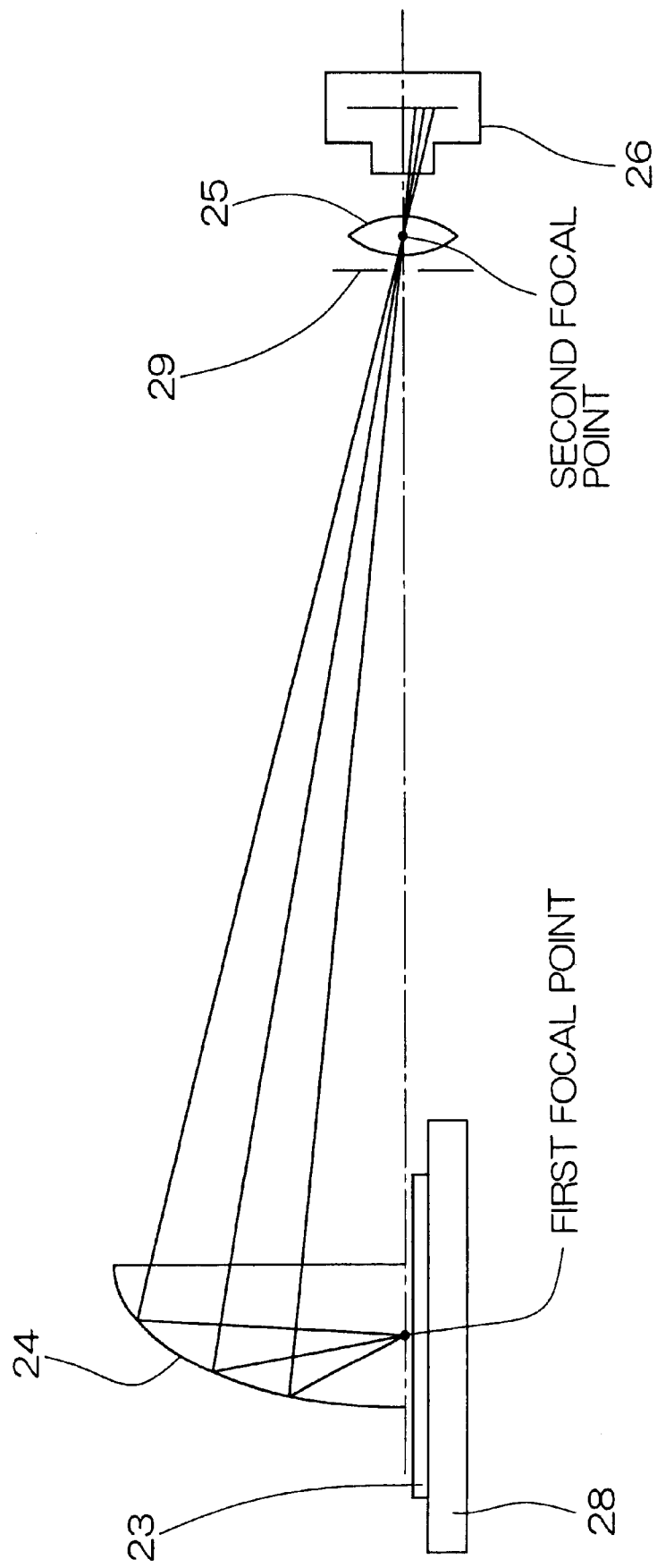
FIG. 12 is a detailed arrangement view illustrating a first specific example of the optical system for measuring the angle characteristics of a sample of the self light-emitting type.

FIG. 12 is a detailed arrangement view illustrating a first specific example of the optical system 21. In this first example, it is assumed that the liquid crystal display element 23 is of the self light-emitting type. An illumination light source is not used for the liquid crystal display element 23 and is therefore not shown in FIG. 12.

The optical system 21 comprises: a stage 28 on and by which the sample 23 is placed and held in an optional posture; an ellipsoidal mirror of revolution 24 for condensing, on the second focal point, the light emitted from the sample 23 disposed in the vicinity of the first focal point; an aperture 29 through which the light reflected by the ellipsoidal mirror of revolution 24 passes; an image-forming lens 25 disposed at the second focal point of the ellipsoidal mirror of revolution 24 for forming the image formed on the surface of the ellipsoidal mirror of revolution 24; and a camera 26 for recording the image formed by the image-forming lens 25. An optical filter may be disposed in front of the camera 26. Examples of the optical filter include a wavelength cutting filter for eliminating the wavelength unnecessary for measurement, a Y-view sensitivity filter for approximating the camera sensitivity to the sensitivity of the human eyes, a light attenuating filter for attenuating the light from the sample, and the like. Further, there may be selected and disposed a tristimulus-value filter for measuring chromaticity and brightness.

There is used the ellipsoidal mirror of revolution 24 having a first focal distance f1 of 55 mm and a second focal distance f2 of 600 mm. A space of 8 mm is assured as the distance between the sample 23 and the lower end surface of the ellipsoidal mirror of revolution 24. It is therefore not required to use special attention for placing the sample 23.

Figure 13:
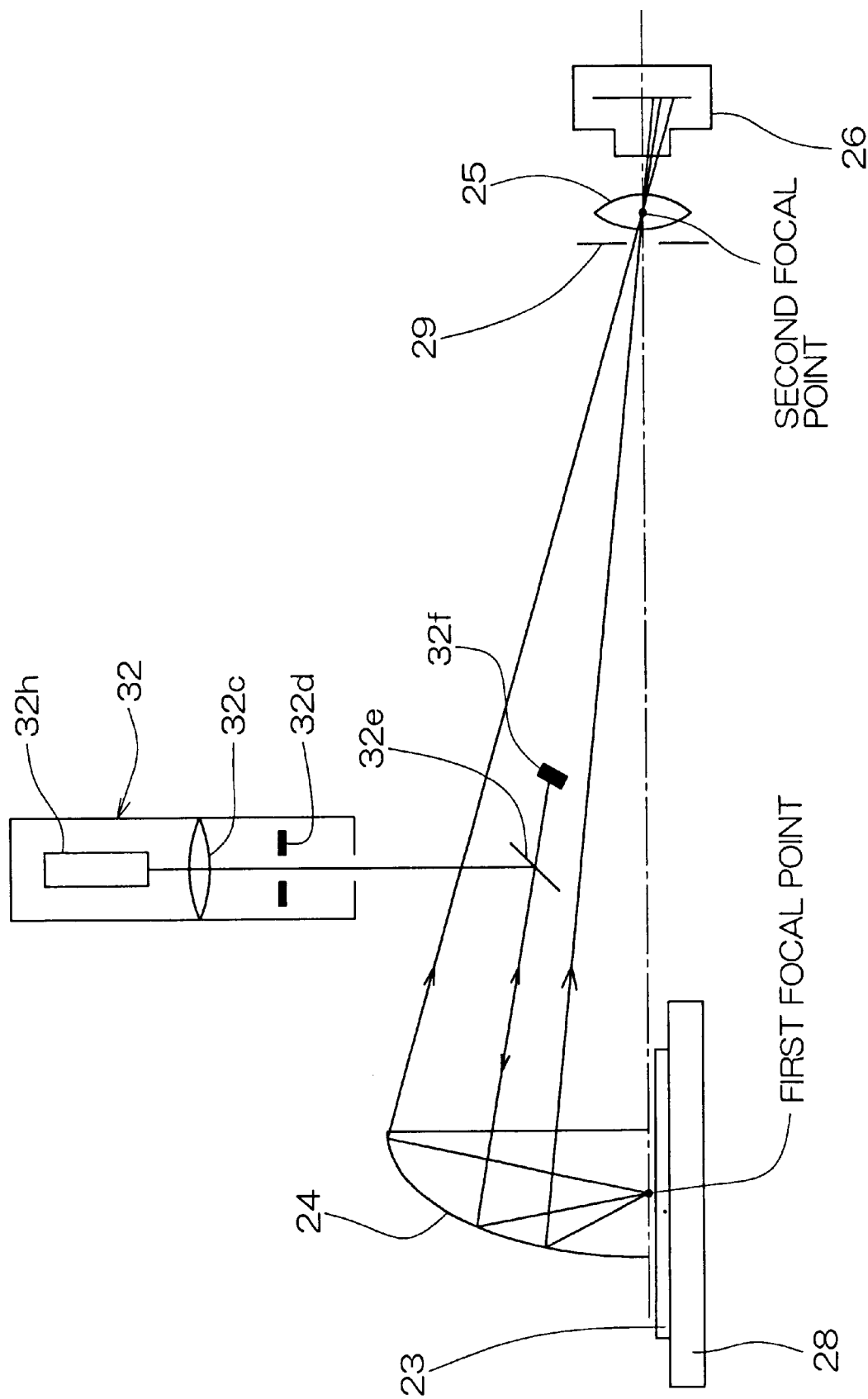
FIG. 13 is a detailed arrangement view illustrating a second specific example of the optical system for measuring the angle characteristics of a sample of the reflection type.

FIG. 13 is a detailed arrangement view illustrating a second specific example of the optical system 21. In the second example, an illumination light source 32 for irradiating light to a liquid crystal display element 23 is used to measure the reflectivity.

This illumination light source 32 comprises a light source 32h, a lens 32c movable on the optical axis, an iris diaphragm 32d disposed at the light emitting side of the lens 32c, and a reflection mirror 32e for projecting the light from the light source 32h, on the first focal point of the ellipsoidal mirror of revolution 24. In FIG. 13, the reflection mirror 32e is positioned such that light from the light source 32h is projected on that point of the ellipsoidal mirror of revolution 24 which is located immediately above (θ=0) its first focal point. However, the reflection mirror 32e can be changed in position and angle such that light from the light source 32h is projected on the ellipsoidal mirror of revolution 24 in the θ range from 0° to several tens of degree.

The lens 32c serves as an adjusting member for condensing the spot of the illumination light source on the sample 23 or on the point of infinity. The spot diameter is minimized when the lens 32c is positioned such that the virtual image of the light source is formed at the position of the second focal point of the ellipsoidal mirror. The opening angle of the illumination light is adjusted by the iris diaphragm 32d.

A light attenuating filter 32f is disposed at the position of regular reflection (In FIG. 13, the light attenuating filter 32f is hidden behind the shadow of the reflection mirror 32e because the angle θ at which the illumination light is incident upon the sample, is 0°). The light attenuating filter 32f serves as a filter (ND filter) for attenuating the light regularly reflected from the sample 23. Such light attenuation reduces the regular reflection component and assures a dynamic range for measurement of a diffusion component.

Figure 14:
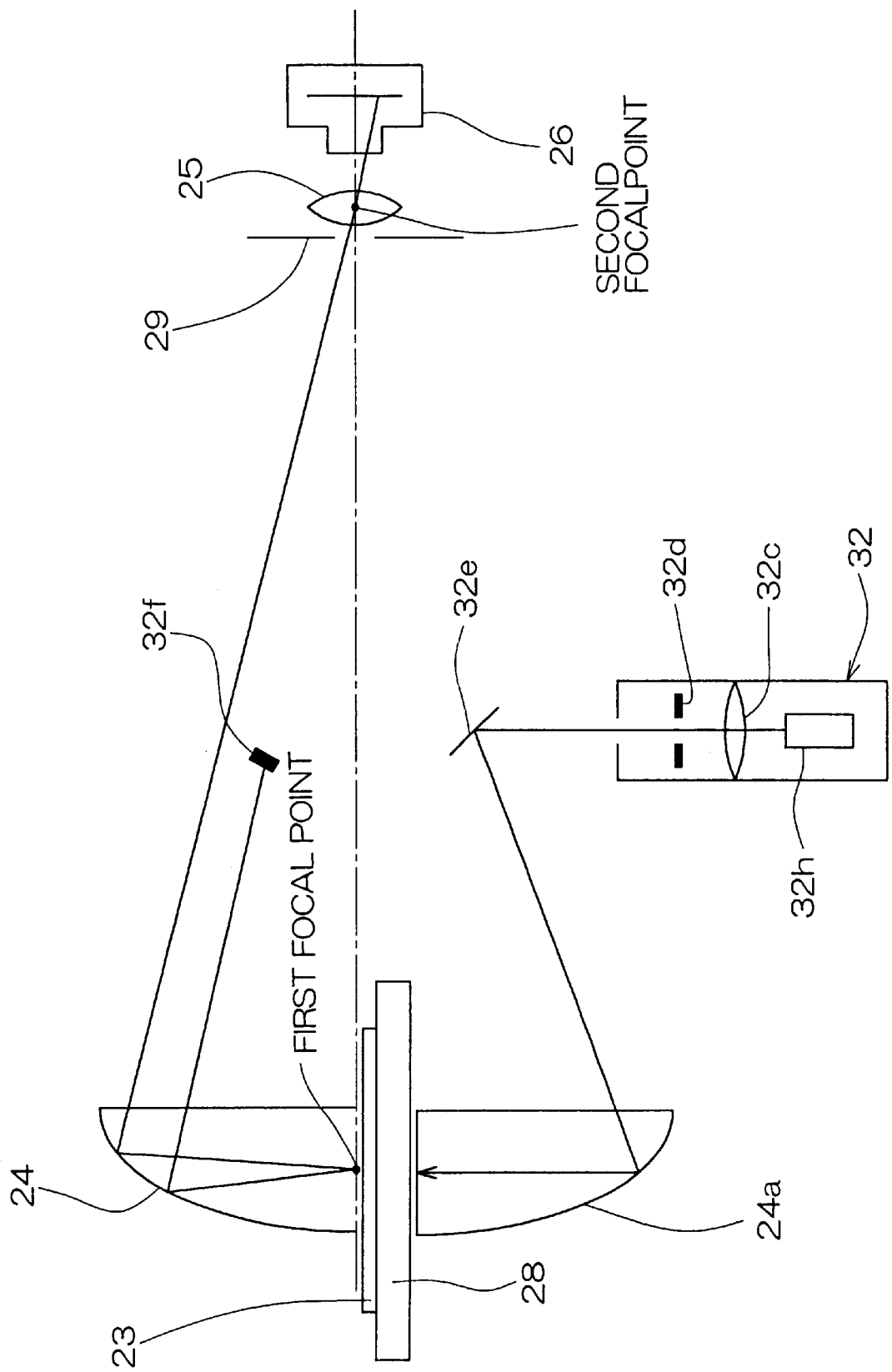
FIG. 14 is a detailed arrangement view illustrating a third specific example of the optical system for measuring the angle characteristics of a sample of the transmission type.

FIG. 14 is a detailed arrangement view illustrating a third specific example of the optical system 21. In this third example, there is disposed the illumination light source 32 for transmittably illuminating the liquid crystal display element 23 from below.

For transmittably illuminating the liquid crystal display element 23 from below, an ellipsoidal mirror 24a is disposed below the stage 28. Together with the light condensing ellipsoidal mirror 24, this ellipsoidal mirror 24a is cut out from a single ellipsoidal mirror. Therefore, the ellipsoidal mirrors 24, 24a have the same focal distances f1, f2. This does not involve the likelihood that the focal points are positionally shifted from each other. In this third example, the illumination light source 32 used in FIG. 13 is used as rotated by an angle of 180° in the opposite direction. By this arrangement, both transmissivity and reflexibility can be measured with one illumination light source 32. This achieves a compact and economical optical angle characteristic measuring apparatus.

In transmissivity measurement, too, when a direct transmitted light is strong, the light attenuating filter 32f is used to assure a dynamic range for measuring a diffusion component.

Figure 15:
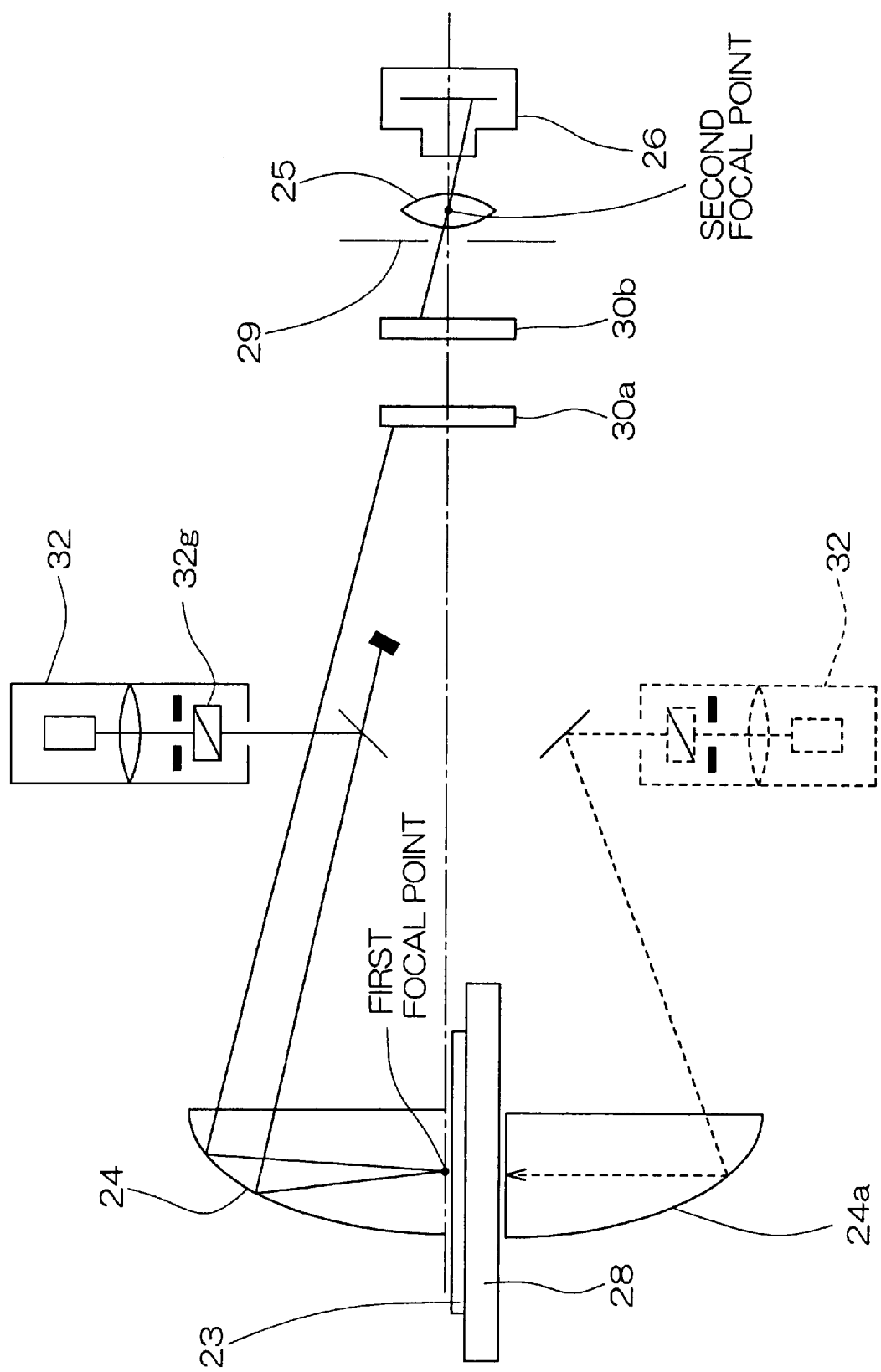
FIG. 15 is a detailed arrangement view illustrating a fourth specific example of the optical system for measuring the polarization angle characteristics of a sample of the reflection or transmission type.

FIG. 15 is a detailed arrangement view illustrating a fourth specific example of the optical system 21. This fourth example is arranged to measure the polarization characteristics of the liquid crystal display element 23. The reflectivity polarization characteristics can be measured when the illumination light source 32 is located in the position of solid lines, and the transmissivity polarization characteristics can be measured when the illumination light source 32 is located in the position of broken lines.

The illumination light source 32 has a polarizer 32g, and a phase-contrast plate 30a and an analyzer 30b are disposed between the ellipsoidal mirror 24 and the image-forming lens 25. Each of the polarizer 32g, the phase-contrast plate 30a and the analyzer 30b is arranged such that its polarization face is rotatable. By setting each of these rotation angles to a predetermined angle, there can be obtained, as a function of visual field angles, physical values such as the ellipticity (tan ø) of polarization of the sample, the phase contrast (cos Δ), the rotation direction of the polarization face.

The polarizer 32g, the phase-contrast plate 30a and the analyzer 30b are so arranged as to be automatically retreated from the optical axis when no polarization characteristics are measured.

What we claim is:

1. An optical angle characteristic measuring apparatus capable of measuring angle distribution of intensity of light emitted from a sample, comprising:

an ellipsoidal mirror having a first focal point and a second focal point, and for reflecting and condensing the emitted light from a sample disposed in the vicinity of the first focal point;

an image-forming lens disposed in the vicinity of the second focal point, at which light reflected from said ellipsoidal mirror converges, for forming, on a record face, an image formed on said ellipsoidal mirror;

an aperture disposed in the vicinity of the second focal point, light reflected from the ellipsoidal mirror passing through the aperture;

a recorder for recording said image formed by said image-forming lens; and;

an illumination light source for transmitting light to the sample, said illumination light source being arranged to transmit light to the sample at an angle substantially normal to an alignment of the lens, aperture and recorder, the sample and the light source being located substantially outside of a space lying between the two focal points.

2. An optical angle characteristic measuring apparatus according to claim 1, wherein said illumination light source is a monochromator for changing the wavelength of light transmitted to the sample.

3. An optical angle characteristic measuring apparatus according to claim 1, wherein light from said illumination light source is reflected from the sample.

4. An optical angle characteristic measuring apparatus according to claim 1, wherein light from said illumination light source is transmitted through the sample.

5. An optical angle characteristic measuring apparatus according to claim 1, further comprising a polarizer for changing the polarization face of light transmitted from said illumination light source, and an analyzer for detecting the polarization of light emitted from the sample.

6. An optical angle characteristic measuring apparatus according to claim 1, wherein said illumination light source transmits light to said sample by reflection from said ellipsoidal mirror.

7. An optical angle characteristic measuring apparatus according to claim 1, wherein said ellipsoidal mirror is replaced by a spherical mirror formed from a portion of a spherical surface, or a conical mirror formed from a portion of a conical surface.

* * * * *